(12) United States Patent
Chawla

(10) Patent No.: US 8,357,329 B1
(45) Date of Patent: Jan. 22, 2013

(54) METHOD AND APPARATUS FOR DESTROYING PATHOGENIC BACTERIA

(75) Inventor: Manmohan S. Chawla, University Park, MD (US)

(73) Assignee: System Planning Corporation, Arlington, VA (US)

( * ) Notice: Subject to any disclaimer, the term of this patent is extended or adjusted under 35 U.S.C. 154(b) by 198 days.

(21) Appl. No.: 12/799,695

(22) Filed: Apr. 30, 2010

(51) Int. Cl.
*A61L 2/00* (2006.01)
*G21B 1/00* (2006.01)
*G21G 1/10* (2006.01)

(52) U.S. Cl. .......................... 422/22; 376/114; 376/190

(58) Field of Classification Search .................. 422/22; 376/114, 156, 190
See application file for complete search history.

(56) References Cited

U.S. PATENT DOCUMENTS 6,925,137 B1 * 8/2005 Forman .......................... 376/190
2002/0172317 A1 * 11/2002 Maksimchuk et al. ....... 376/190

* cited by examiner

*Primary Examiner* — Kevin Joyner

(57) ABSTRACT

An apparatus for destroying bacteria is provided which includes a neutron generator and a target polymer film which will receive the impact of neutron emissions. Neutrons impacting the target film produce a second emission of high energy protons which are made to move through an electromagnetic field external to the neutron tube thereby accelerating and steering a generated proton spray. This embodiment is well-suited for treating physical locations known to be infected by pathogenic microorganisms.

5 Claims, 4 Drawing Sheets

METHOD AND APPARATUS FOR DESTROYING PATHOGENIC BACTERIA

BACKGROUND OF THE INVENTION

1. Field of the Invention

Figure 1:
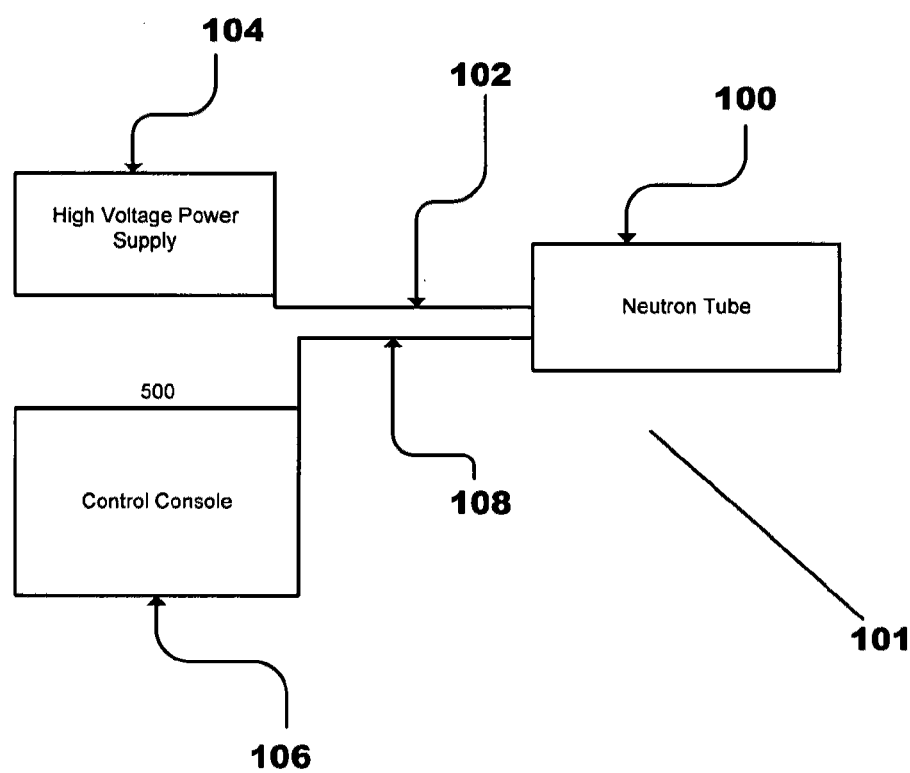
Figure 2:
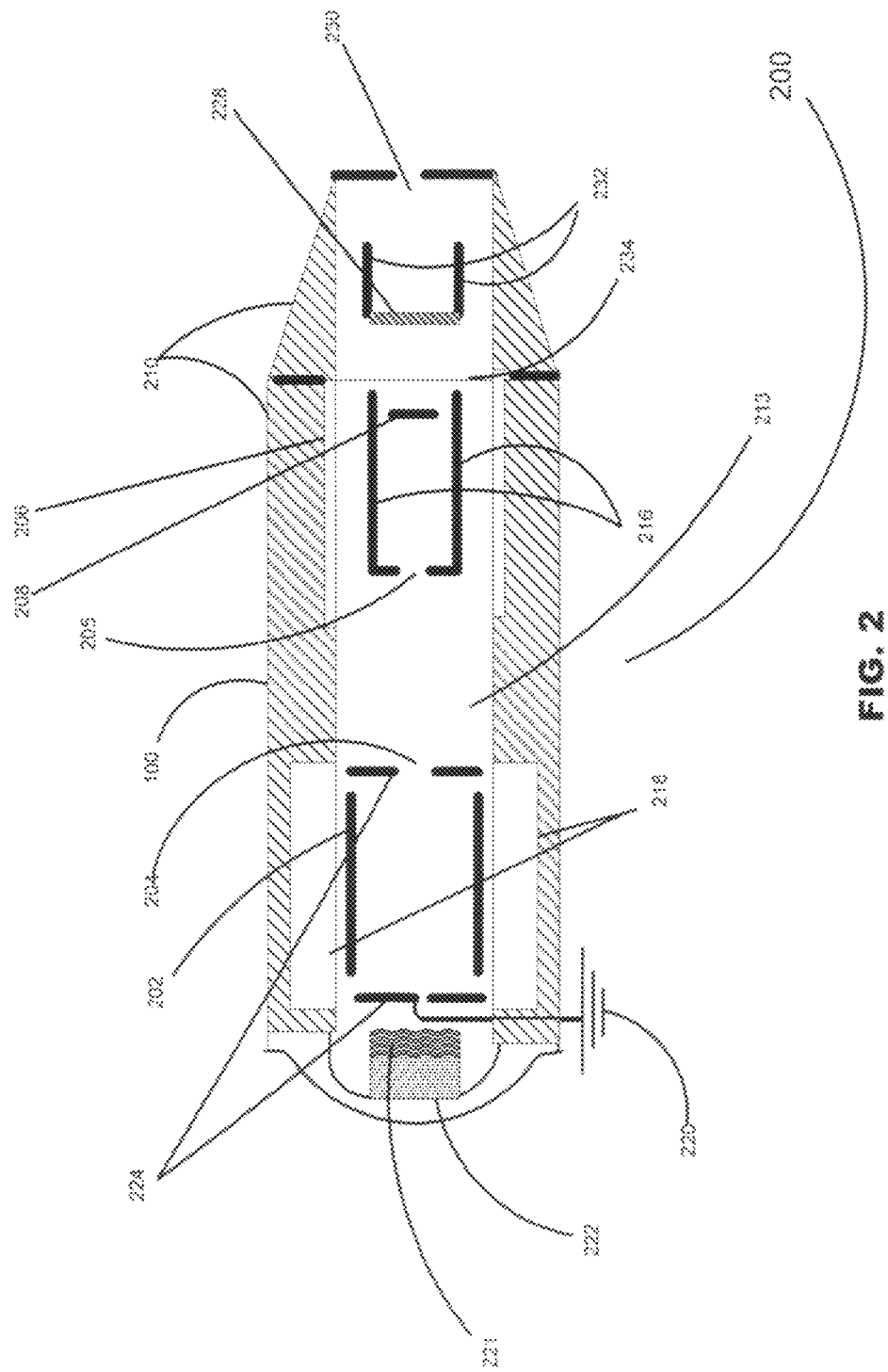
Figure 3:
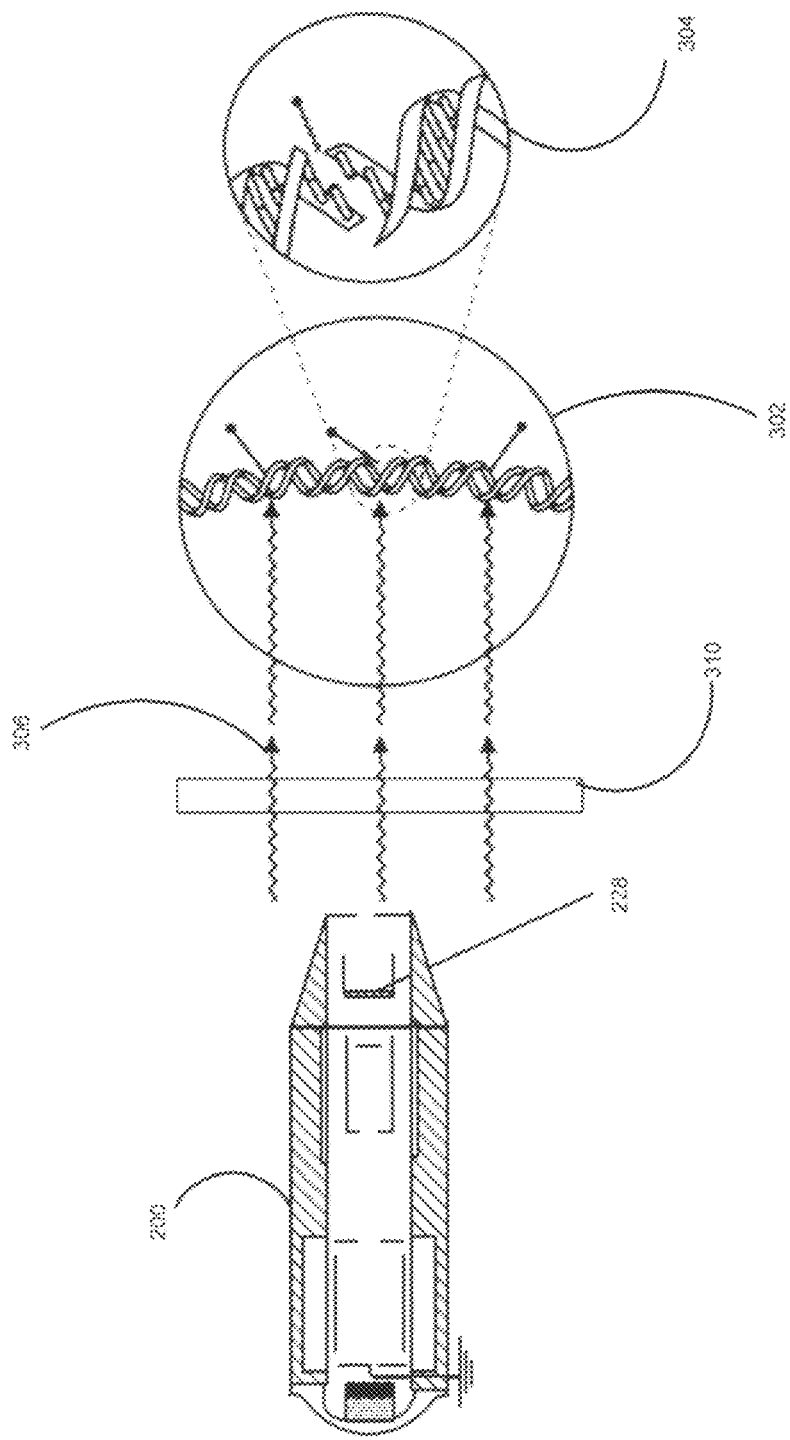
Figure 4:
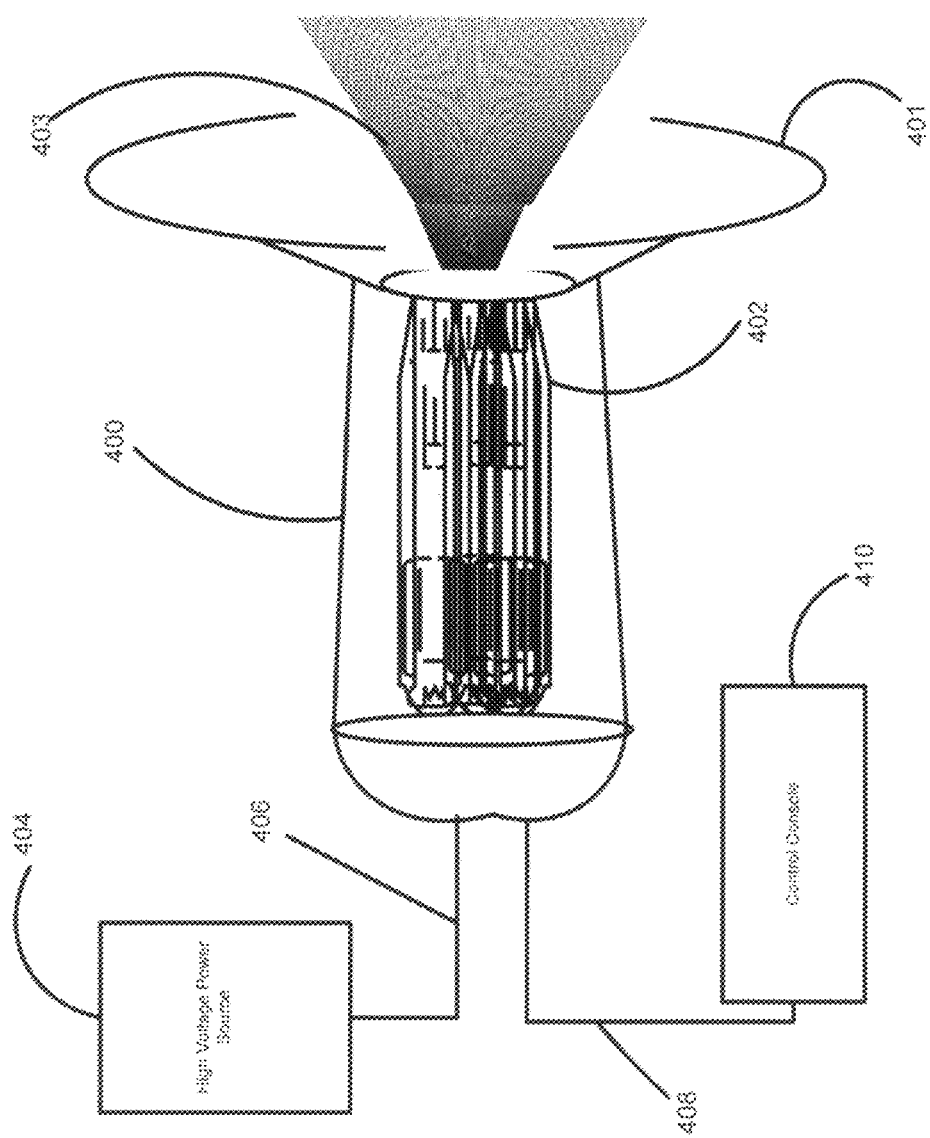

The present invention relates to destroying pathogenic bacteria and harmful microorganisms. More particularly, the present invention relates to an apparatus and method for generating protons from a neutron tube for the purpose of killing pathogenic bacteria and other harmful microorganisms.

2. Description of Related Art

A bioterrorism attack is the deliberate release of viruses, bacteria, or other germs (agents) used to cause illness or death in people, animals or plants. There are three types of agents classified by the US government as bio agents: categories A, B, and C. Category A agents are high priority agents posing a risk to national security, can be easily transmitted and disseminated, result in high mortality, have potential major public health impact, may cause public panic, and require special action for public health preparedness. Category B agents are moderately easy to disseminate and have low mortality rates. Category C agents are emerging pathogens that might be engineered for mass dissemination due to easy production and dissemination or possessing the capability of inflicting high mortality rates and major health impact.

Four of the six bio agents classified as Category A are bacterium. Botulism toxin is one of the deadliest toxins known and is produced by the bacterium *Clostridum botulinum*. Botulism supplies are readily available worldwide due to its cosmetic applications in injections. Bubonic plague is a disease caused by *Yersinia pestis* bacterium. Historically spread via rodent hosts, the disease is transmitted to humans by flea bites or by aerosol in the form of pneumonic plague in which form a weaponized threat could be deployed. Tularemia, or rabbit fever, is caused by the *Francisella tularensis* bacterium and although it has a very low fatality rate, can severely incapacitate its victims. Anthrax is another deadly form of bacteria, *Bacillus anthracis*, classified as a Category A bio agent.

The three common methods used for removing bacteria and other harmful microorganisms are fumigation, liquid bleach, and ultraviolet-light. With respect to fumigation, acceptable results have been achieved using industrial scale chlorine oxide gas. Another effective fumigation agent includes $CH_3Br$ as described by Kolbe et al. Despite some effectiveness, however, fumigation has several disadvantages. For instance, fumigation requires evacuation of the premises, use of protective gear by all operators, and a relatively long time for application of product, dissipation of poisonous gas fumes, and post application cleanup. Comparatively, while the use of liquid bleach is less expensive, it is also less effective on porous surfaces. Furthermore, on items such as upholstery, papers, books, wood surfaces, using bleach not only decontaminates objects but it also destroys them. Further, liquid bleach generally results in a less complete coverage of a targeted site. Alternatively, radiating with ultraviolet light from x-ray equipment provides good coverage but is expensive and difficult for field use. Nonetheless, a large facility has been constructed by Ion Beam Applications in Bridgeport, N.J. for the purpose of treating US mail against the threat of anthrax at a cost of several millions of dollars. In addition to the expense of owning and operating such a facility, there is the time, expense, inconvenience and public safety hazard of shipping contaminated materials to a fixed facility for decontamination.

Even when treated by conventional methods, dormant bacteria in the form of spores can exist in the inert state for a very long time. Endospores ensure the survival of bacterium through periods of environmental stress. They are therefore resistant to ultraviolet and gamma radiation, desiccation, lysozyme, temperature, starvation, and chemical disinfectants. An endospore is a non-reproductive structure that forms when a bacterium produces a thick internal wall that encloses its DNA and part of its cytoplasm. This DNA is capable of surviving most conventional cleaning methods.

Beyond the conventional methods, several alternative methods of destroying bacteria have been proposed. For instance, atomic oxygen, $O^{15}$ and $O^{16}$, are known to be very effective against bacteria and many uses have been described in the recent past. However, each of these devices is limited and cannot produce energetic ions. Further, the treatment generally leaves large scars or burn marks on the treated surfaces.

Use of ozone has also been suggested. A company, O3Co, in Idaho has developed a process for delivering a high concentration of ozone for destroying bacteria. This requires sealing up an area to be cleaned and an exposure time of sixty minutes.

A British Company, BioQuell, employs hydrogen peroxide for decontamination of hospital wards and patient rooms. The treatment is effective against walls, beds, furniture, medical equipment and various touch screens. However, the gas is corrosive, the equipment is expensive and the resulting water vapors necessitate a drying cycle.

The use of neutrons for killing anthrax spores is advocated by Liu and Wang. They employ a strong radioactive source $^{235}Cf$ to produce $10^{12}$ neutrons per second in the 2.3 MeV range. Neutrons are significantly more effective in penetrating and destroying bacteria, however, the strong radioactivity of the source and its half-life of 2.3 years is a concern. The fielding of the radioactive source is also a great logistical burden to the user.

Carnegie Mellon researchers, Colin Horwitz et al, have described the use of a nano-catalyst composed of iron and tetra amido macrocyclic ligand (Fe-TAML) in a spray of sodium carbonate and bicarbonates, followed by an oxidizing agent, butyl hydro peroxide. This method is effective but it requires extensive cleanup after the treatment.

Still another method of killing bacteria is described by Ouellete ("Femtosecond Lasers Prepare To Break Out of the Laboratory" Physics Today, Vo. 17, No. 1, pages 36-38, January 2008.") This method, however, is less effective at killing bacteria spread over large areas and it requires significant amounts of energy.

In the end, none of the prior art discloses an effective and efficient way to destroy *Bacillus anthracis, Staphylococcus aureus* or any other pathogenic bacteria or other harmful encapsulated nucleic microorganism. Therefore, a need exists to develop a novel alternative that can kill microorganisms without the drawbacks evident in the prior art.

SUMMARY OF THE INVENTION

The object of the present invention is to overcome the shortcomings disclosed in the prior art. To achieve this object, the present invention provides an apparatus for destroying bacteria which includes a neutron generator and a target jacket polymer film which receives the impact of neutron emissions. The target jacket film produces a second emission of high energy protons which move through an electromagnetic field external to a neutron tube and focus electrode which accelerate and steer the protons to generate a proton spray. This embodiment is well-suited for treating physical locations known to be infected by pathogenic microorganisms.

There are several advantages found in one or more aspects of the present invention over the prior art. For instance, the apparatus of the present invention can be quickly deployed directly to an infected location. Further, the present invention does not require the use of bulky shielding devices and gas masks. Additionally, the present invention is relatively inexpensive when compared to conventional large facilities currently in use to irradiate infected bulk items.

A further advantage of the present invention is that it provides a much higher kill rate of highly resistant pathogenic bacteria. Effectiveness is increased a hundred fold over the conventional use of chemical, liquid form bactericide in commercial use. Further, by inflicting kinetic energy damage to cell walls and cell interiors, the bacteria is destroyed while minimizing damage to other material. Still further, because the proton emissions from one or more aspects of the present invention can be focused, accelerated, and steered to the target areas, the present invention is highly effective against a wide variety of resistant bacteria and bacillus endospore. Residual neutron emissions can also aid in destroying encapsulated microorganisms.

The accompanying drawings, which are incorporated in and constitute part of the specification, illustrate various embodiments of the invention and together with the description, serve to explain the principles of the invention.

BRIEF DESCRIPTION OF THE DRAWINGS

FIG. 1 shows an example of a neutron generator as known in the prior art.

FIG. 2 shows first preferred embodiment of the present invention.

FIG. 3 shows the first preferred embodiment of the invention directing radiation against a bacterial cell.

FIG. 4 shows a further preferred embodiment of the present invention.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended and further applications of the principles of the invention are contemplated as would normally occur to one skilled in the art to which the invention relates.

FIG. 1 generally illustrates an exemplary neutron generator configuration for use with the present invention. As shown, a neutron generator 101 generally includes a neutron tube 100 connected to an external high voltage power supply 104 via high voltage cables 102. As further shown, such a neutron generator 101 may generally include a control console 106 connected to the neutron tube 100 via control cables 108 which allow an operator to adjust the operating parameters of the neutron tube 100. In operation, neutrons are produced by the neutron generator 101 creating deuterium ions and accelerating those ions into a target that contains tritium or deuterium. The deuterium-tritium reaction is used only in special circumstances because although the neutron yield from the deuterium-tritium reaction yields approximately 100 times more neutrons, the energetic neutrons from deuterium-tritium reaction are less effective in neutralizing bacteria. Example reactions which take place in the neutron tube are: $D+^2H$ yields $n+^3He$, $E_n=2.5$ MeV and $D+^3H$ yields $n+^4He$, $E_n=14.2$ MeV. Neutrons produced from the D-T ($D+^3H$) reaction are emitted uniformly in all directions from the target. Neutron emissions from the D-D ($D+^2H$) reaction is slightly peaked along the axis of the ion beam direction. In both cases, a He nucleus ($\alpha$ particle) is emitted in the exact opposite direction of the neutron. The neutron tube 100 which encloses the ion source, ion optics, and accelerating electrode is preferably a vacuum tight metal housing which employs heavy duty dielectrics to insulate the high voltage elements of the tube.

With reference now to FIG. 2, a cross sectional view of an exemplary neutron tube 100 for use with the present invention 200 will be detailed. As shown, a neutron tube 100 may include a Penning ion source 220, a deuteron gas supply 222, a heating element 221 a permanent magnet 218, a source cathode 224, an ion source anode 202, a deuteron ion exit 204, an accelerating electrode 216, a deuteron entrance 205, a dielectric insulator 206, a deuterated target 208, a vacuum 213, neutron tube top 234, a poly methyl methacrylate (PMMA) or polyethylene absorptive jacket 210, a second target 228, a proton accelerating electrode 232, and a proton exit 230. According to a preferred embodiment of the present invention, the second target 228 is preferably comprised of poly methyl methacrylate (PMMA) for producing high energy protons. Alternatively, the second target 228 may be comprised of a thin sheet of polyethylene for producing high energy protons.

With reference now to FIGS. 2 and 3, the preferred method for use of the present invention will now be discussed. In operation, the neutron tube 100 generates ions from Penning ion source 220 which is a low gas pressure cold cathode ion source. The ion source anode 202 is preferably at a positive potential, either direct current (dc) or pulsed with respect to the source cathode 224. The ion source voltage is preferably between 2 and 7 kilovolts. A magnetic field oriented parallel to the source axis is produced by permanent magnet 218. The gas pressure in the source is regulated by heating 221 and the reservoir element 222. A plasma is formed along the axis of the anode 202 which traps electrons which in turn further ionizes gas in the source. The ions are extracted through an exit cathode 204. Under normal operation, the ion species produced by the Penning Source 220 are preferably over 90% molecular ions.

Ions emerging from the exit cathode 204 are accelerated through the potential difference between the exit cathode 204 and the accelerator electrode 206. Preferably, the exit cathode 204 is at ground potential and the target is at a high (negative) potential. The accelerating electrode 206 is preferably 100-200 kV (negative) with respect to the exit cathode 204. The ions pass through the accelerator electrode 206 and strike a deuterated target 208. A vacuum envelope 213 insulates the high voltage activity in the neutron tube 100. To deliver maximum flux to a sample, the neutron tube 100 is preferably operated with the deuterated target 208 grounded and the source floating at high (positive) potential. The accelerator voltage 216 is preferably between 80-180 kV, meaning the polarity of the deuterated target 208 with respect to the ion source can be changed from negative to positive depending upon neutron beam properties.

Thereafter, the accelerated deuteron ions strike the deuterated target 208 emitting 2.5 MeV neutrons in the D-D reactions or 14.5 MeV neutrons in the D-T reaction. The deuterated target 208 is preferably a thin film of metal such as titanium, scandium, or zirconium which may be deposited on a copper or molybdenum substrate. Titanium, scandium or zirconium form stable chemical compounds called metal hydrides when combined with hydrogen or its isotopes. These metal hydrides are made up of two hydrogen (deuterium or tritium) atoms per metal atom and allow the deuterated target 208 to have extremely high densities of hydrogen maximizing the neutron yield of the neutron tube 100. The gas reservoir 222 also uses metal hydrides as the active material. Preferably, the neutron tubes 100 are designed such that the gas reservoir element 222 and the deuterated target 208 each incorporate equal amounts of deuterium and tritium.

As discussed above, the target 228 is preferably comprised of poly methyl methacrylate (PMMA) or polyethylene. The high hydrogen content of these polymers, acts as an abundant source of protons. When high energy neutrons from the neutron tube 100 impact the hydrogen atoms in the polyethylene target or PMMA target 228, protons are displaced from the material transferring all of the energy of the neutrons to the ejected protons. A second accelerator electrode 232 may be used to control the speed of the proton spray. In this way, protons can be focused, accelerated, and steered.

With respect to the energy of the proton spray, since the neutron can impact the proton at any angle, the energy of the recoil proton will vary from 0 to 2.5 MeV with an average of 1.25 MeV. The proton after traveling several inches in the air is capable of penetrating almost 50 microns in depth and destroying layers of *Bacillus anthracis* or *Staphylococcus aureus* which are roughly the size of one micron.

The absorptive thick layer of hydrogenous material 210 or neutron absorbing material assist to stop or convert neutrons traveling backwards or sideways. Neutrons that are not converted into protons, having a forward bias, though not as effective as protons, may exit via proton exit 230 and thereby also assist in destroying bacteria.

Now with reference to FIG. 3, the operation of the proton source 200 is further illustrated. As shown, ionizing radiation 306 penetrates a physical barrier 310 (such as cloth or other covering) before penetrating cell wall 302 and breaking the DNA bonds 304 thus eradicating pathogenic bacterium. Each 1.25 MeV proton generated by the interaction of the 2.5 MeV neutron and hydrogenous PMMA target film 228 or polyethylene target film 228 will deposit approximately 0.06 MeV (1 MeV=$10^{-13}$ J) in a cell. However, only a small fraction of this energy or 0.1155 gray unit (Gy) is absorbed by the bacterium (1 Gy=1 J/kg) with 1000 Gy considered a lethal dose. Accordingly, 1000 Gy of energy will be deposited in each bacterium using the neutron generator of the present invention which preferably generates $10^{10}$ neutrons/second.

According to a third preferred embodiment of the present invention, the target film 228 may alternatively be comprised of a thin layer of $U^{235}$ deposited on a thin metal like aluminum as a target film. The bombardment of neutrons on $U^{235}$ aluminum substrate target film jacket will produce spontaneous energetic fission fragments which upon impact will also destroy highly resistant bacteria and bacillus endospore. This aspect of the invention also requires thermilization of neutrons.

According to a fourth preferred embodiment of the present invention, the target film 228 may alternatively be comprised of a thin layer of boron incorporated on an aluminum or copper substrate. The bombardment of neutrons on a boron/aluminum substrate target film or a boron/copper substrate target film will produce alpha-particles at 2.4 MeV which upon impact will also be highly effective in destroying highly resistant bacteria. This aspect of the invention also requires thermilization of neutrons.

With reference now to FIG. 4, a further example of the present invention is provided. In this example, a plurality of proton sources 402 are arranged and operated as one unit 400 from a control console 410 connected by reservoir cable 408. The plurality of proton sources 402 are powered by a sufficient high voltage power source 404 connected by high voltage power cables 406. This configuration may apply a larger coverage of protons effective in a larger target location. The neutron absorptive collar 401 would provide a uniform barrier which would absorb neutrons traveling in a direction other than a forward bias.

In addition to killing pathogenic bacteria, the present invention may also be applied to basements and carpets in order to destroy mold and fungus. The present invention may also be adapted for use in water purification systems and pasteurization processes.

As detailed herein, the present invention provides a reliable, lightweight, and relatively inexpensive means of eradicating deadly pathogenic bacterium such as *Bacillus anthracis* and *Staphylococcus aureus* and provides a more effective rate of kill than ultraviolet light, x-rays, or gamma rays. Furthermore, the present invention is able to consistently produce high yields of energetic protons from benign materials such as polyethylene and poly methyl methacrylate which significantly reduces the effects of radiation exposure when compared to the strong radioactive sources such as $Cf^{235}$ currently employed in neutron production.

While the above description contains much specificity, these should not be construed as limitations on the scope, but rather as examples. Many other variations are possible. For example, an embodiment of the proton source with an external electromagnetic field may be devised to focus a diverging beam of protons on an infected area. Still further, the present invention could include an external electromagnetic field devised to steer the proton beam for wider coverage of a target area by allowing the proton beam to move rather than the apparatus. As described above, adaptation of the present invention for use in water purification systems, pasteurization processes, and mold and fungus treatments are also alternative embodiments of the invention. Accordingly, the scope should be determined not by the embodiments illustrated, but by the appended claims and their legal equivalents.

I claim:

1. An apparatus for destroying bacteria, the apparatus comprising:
- an ion generator for generating positively charged deuteron ions;
- a neutron generator comprising a deuterated target, wherein the neutron generator directs the positive deuteron ions to impact the deuterated target to generate neutrons;
- a proton generator comprising a target element, wherein the proton generator directs that neutrons to impact the target element to generate the protons; and
- a focusing element for focusing, accelerating and steering protons to a desired location.

2. The apparatus as recited in claim 1, wherein the deuterated target is selected from the group consisting of:
- a target comprising hydrogenous poly methyl methacrylate (PMMA);
- a target comprising polyethylene;
- a target comprising uranium (U235) deposited on an aluminum substrate; and
- a target comprising boron deposited on a metal substrate.

3. The apparatus as recited in claim 1, wherein the apparatus further comprises a control element for creating a pulsed beam of protons for destroying bacteria.

4. A method of destroying bacteria, the method comprising the steps of:

generating positively charged deuteron ions;

accelerating the positive deuteron ions to impact a deuterated target to produce neutrons;

directing the neutrons to impact a target element to produce high energy protons; and focusing the high energy protons against bacteria.

5. The method of claim 4, wherein the target element is selected from the group consisting of:

a target comprising hydrogenous poly methyl methacrylate (PMMA);

a target comprising polyethylene;

a target comprising uranium (U235) deposited on an aluminum substrate; and a target comprising boron deposited on a metal substrate.

* * * * *